(12) United States Patent
Katayama et al.

(10) Patent No.: US 7,276,376 B2
(45) Date of Patent: Oct. 2, 2007

(54) ANALYZING METHOD OF A BLOOD COAGULATION REACTION

(75) Inventors: Masayuki Katayama, Miki (JP);
Susumu Hoshiko, Kobe (JP);
Takayoshi Izumi, Kobe (JP); Yoshihiro Mishima, Kobe (JP); Wilfried Meyers, Marburg (DE); Norbert Zander, Marburg (DE)

(73) Assignees: Sysmex Corporation, Kobe-shi, Hyogo (JP); Dade Behring Marburg GmbH, Marburg (DE)

( * ) Notice: Subject to any disclaimer, the term of this patent is extended or adjusted under 35 U.S.C. 154(b) by 664 days.

(21) Appl. No.: 10/307,922

(22) Filed: Dec. 3, 2002

(65) Prior Publication Data

US 2003/0138962 A1    Jul. 24, 2003

(30) Foreign Application Priority Data

Dec. 3, 2001    (JP) .............................. 2001-369206

(51) Int. Cl.
*G01N 33/86* (2006.01)

(52) U.S. Cl. ..................... 436/69; 436/63; 436/164; 73/64.41; 73/64.43; 600/369; 435/13

(58) Field of Classification Search ................. 436/69, 436/164, 63; 73/64.41, 64.43; 600/369; 435/13
See application file for complete search history.

(56) References Cited

U.S. PATENT DOCUMENTS

| | | | | |
|---|---|---|---|---|
| 3,963,349 A | * | 6/1976 | Albright et al. | ............ 73/64.41 |
| 4,217,107 A | * | 8/1980 | Saito et al. | .................... 436/69 |
| 4,876,069 A | | 10/1989 | Jochimsen | |
| 5,284,624 A | | 2/1994 | Behnk | |
| 5,716,796 A | | 2/1998 | Bull et al. | |

FOREIGN PATENT DOCUMENTS

| | | |
|---|---|---|
| DE | 3127560 A1 | 2/1983 |
| JP | 63305255 A | 12/1988 |

* cited by examiner

*Primary Examiner*—Maureen M. Wallenhorst
(74) *Attorney, Agent, or Firm*—Birch, Stewart, Kolasch & Birch, LLP

(57) ABSTRACT

An analyzing method of a blood coagulation reaction by detecting an optical change of a blood sample with an elapse of time, the method includes: setting at least one checkpoint or check region between a starting point of the blood coagulation reaction and the endpoint thereof; and monitoring a reaction state of the blood coagulation reaction at the checkpoint or in the check region to detect an abnormality of the blood coagulation reaction.

12 Claims, 9 Drawing Sheets

ANALYZING METHOD OF A BLOOD COAGULATION REACTION

CROSS-REFERENCE TO RELATED APPLICATION

This application is related to Japanese Patent Application No. 2001-369206 filed on Dec. 3, 2001, whose priority is claimed under 35 USC §119, the disclosure of which is incorporated by reference in its entirety.

BACKGROUND OF THE INVENTION

1. Field of the Invention

The present invention relates to an analyzing method of a blood coagulation reaction. More particularly the invention relates to an analyzing method of a blood coagulation reaction for measuring a blood coagulation time, the method being capable of detecting abnormality in the blood coagulation reaction.

2. Description of Related Art

Blood coagulation detection methods include the method of detecting the increase in viscosity (viscosity detection method), the method of detecting turbidity (turbidity detection method), and their combined method.

In the viscosity detection method, a bar-shaped or spherical magnetic element is placed in the plasma specimen, and a coagulation reagent is added. The motion of the magnetic element becomes slower due to coagulation, and this slowing down is detected.

However, The viscosity detection method produces variable results depending on the shape of the fibrin clumps which are the final product of blood coagulation (that is, the quantity or viscosity of the fibrin). Furthermore, it is impossible to detect coagulation unless the viscosity increases to above a specific level. Besides, because the measurement principle is based on observing the motion of the magnetic element, it is dependent on the strength of the magnetic field of the element.

The turbidity detection method involves mixing the plasma specimen and coagulation reagent, and it does not require a magnetic element or the like. The method can be the transmitted light detection method or the scattered light detection method. With these methods of detection, if the fibrinogen quantity is small, the change in the quantity of transmitted or scattered light can be detected, and it is hence free from the shortcoming of the viscosity detection method.

Methods for analyzing a blood coagulation point include: (1) a percentage detection method; (2) a differential method; (3) a double differential method; (4) an inflection point method; (5) a fluctuation detection method and the like. Among them, in the percentage detection method, the blood coagulation point is detected as a point showing a 50% optical change amount relative to the optical change amount when the blood coagulation finishes, at which point an optical change rate per a unit time is the largest and the rate of polymerization reaction of fibrin monomers is high. Thereby more precise coagulation measurement can be performed for samples such as low fibrinogen samples, chyle samples and laked blood samples.

Normally, for analyzing a blood coagulation reaction, plasma is mixed with a blood coagulation reagent to start the blood coagulation reaction, and the degree of turbidity during the process of the plasma coagulating, that is, during the process of fibrin formation, is detected as a change of the intensity of a signal by an optical detector. If the optical detector is of a scattered light detection system, such a change is represented with time plotted in abscissa and the scattered light amount (intensity) plotted in ordinate, for example, as shown in FIG. 1.

Point A in FIG. 1 indicates a time when plasma is mixed with a coagulation reagent to start the blood coagulation reaction. Then, the blood coagulation reaction advances through a cascade reaction. As stable fobrous fibrin is formed by fibrinogen in the plasma, a change appears in the amount of scattered light (point B). As the formation of the stable fibrin advances, the amount of the scattered light increases. When most of fibrinogen is consumed, the amount of scattered light does not change any more and the blood coagulation reaction terminates (point C). Supposing that the amount of the scattered light at point B is taken as 0% (non-coagulation level) and the amount of scattered light at point C is taken as 100%, a blood coagulation time may be defined as a point where the amount of the scattered light reaches 50% (point T). ΔH is indicative of a change of the amount of scattered light from the start of the blood coagulation reaction to the termination thereof.

Typically, the following complicated process leads to the formation of fibrin. The blood coagulation progresses by two pathways in general: One pathway is called as an extrinsic pathway, through which, starting with tissue thromboplastine discharged from epidermic cells and the like, the coagulation factor VII is activated, which in turn activates the coagulation factor X, then, the activation of the coagulation factor V and the factor II occurs, and finally, fibrinogen is transformed into fibrin. In general, the strength or weakness, that is, the normality or abnormality, of the blood coagulation reaction through this pathway is judged by measuring a "prothrombin time (PT)."

The other pathway is referred to as an intrinsic coagulation, through which the coagulation factor XII is activated by contacting the surface of a solid phase having a negative charge and then activates the factor XI, the activated factor XI in turn activates the factor IX, and further, the activated factor IX activates the factor X with collaborative action of calcium ions and the factor VIII, then, the activation of the factor V and the factor II occurs, and finally, fibrinogen is transformed into fibrin. In general, the strength or weakness, that is, the normality or abnormality, of the blood coagulation reaction through this pathway is judged by measuring an "activated partial thromboplastine time (APTT)," a "partial thromboplastine time (PTT)."

In addition, at the final stage of the coagulation reaction, fibrinogen is required to be transformed into fibrin, whereby the coagulation completes.

As described above, the blood coagulation is a multiple-stage reaction, and thus, when abnormality occurs with the reaction pathways, unstable behavior may be expressed. For example, the reaction falls in such a state as if the reaction apparently stops temporarily in the middle of the reaction (an optical change is not observed), or alternatively, a gradual optical change is observed immediately after the blood coagulation reagent is introduced into plasma. Thus there are cases in which the reaction curve as shown in FIG. 1 is not always produced.

As an example, in the case where the coagulation time is measured based on an optical change amount with respect to high fibrinogen samples collected from heparin-administered patients, APTT sometimes tends to be extremely short. It is considered that such samples exhibit a two-bump reaction (the blood coagulation curve has two increase phases) due to a coagulation reaction caused by an extrinsic sthenia state as shown in FIG. 2: The optical change amount of the samples gradually increases with an elapse of time from the initial stage of the reaction, and then the optical change amount is larger than that of a normal coagulation reaction (second stage). As a result of such behavior different from usual, an incorrect coagulation time is considered to be computed.

SUMMARY OF THE INVENTION

Therefore, it is an object of the present invention to provide a method of analyzing a blood coagulation reaction capable of precisely detecting abnormality in the blood coagulation reaction including abnormality at the initial stage of the reaction as described above.

According to the present invention, it is provided an analyzing method of a blood coagulation reaction by detecting an optical change of a blood sample with an elapse of time, the method comprising:

setting at least one checkpoint or check region between a starting point of the blood coagulation reaction and the endpoint thereof; and monitoring a reaction state of the blood coagulation reaction at the checkpoint or in the check region to detect an abnormality of the blood coagulation reaction.

DESCRIPTION OF THE PREFERRED EMBODIMENTS

Figure 1:
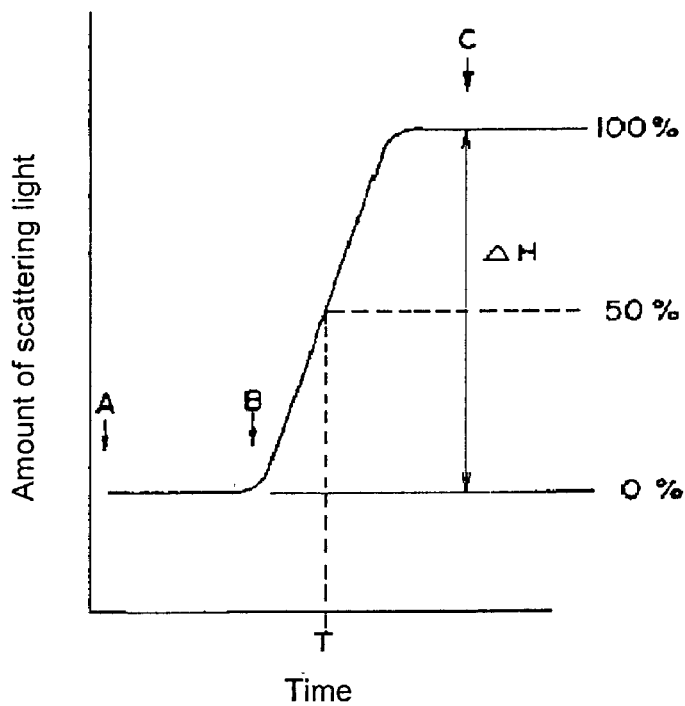
FIG. 1 is a view showing a change of scattered light due to a coagulation reaction.
Figure 2:
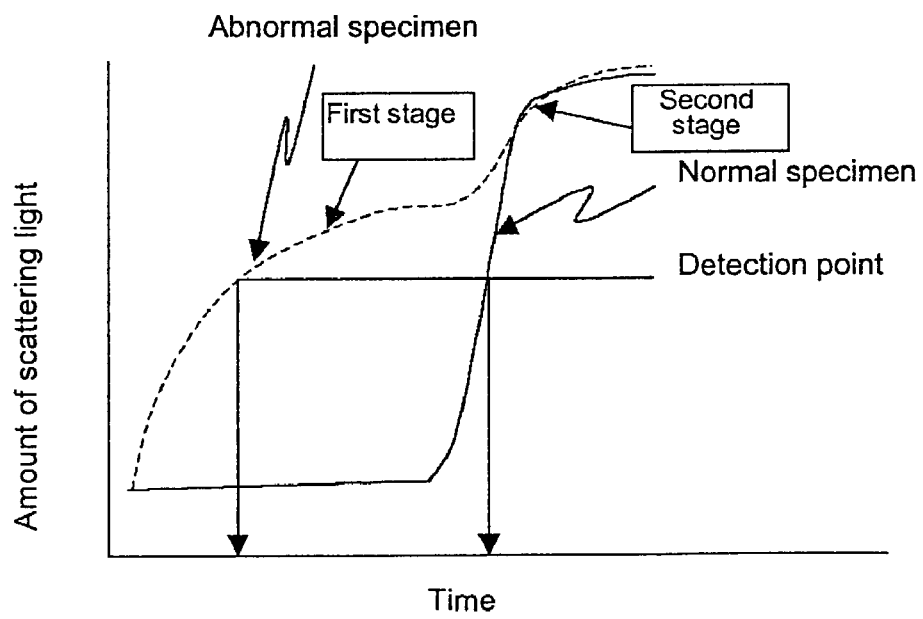
FIG. 2 is a view showing a change of scattered light from a sample which indicates abnormality in an initial stage of the blood coagulation reaction.

The blood sample in the present invention means plasma or diluted plasma separated from blood of mammals including human beings.

For starting a coagulation reaction, the blood sample is mixed with a coagulation reagent which can initiate the coagulation reaction by being added to the blood sample and is used for measuring a blood coagulation time. Different kinds of reagents may be used depending on what type of a blood coagulation time is to be measured. For example, reagents for PT (prothrombin time) measurement or APTT (activated partial thromboplastine time) measurement, and Fbg (fibrinogen amount) measurement can be employed.

In the present invention, an optical change of the blood sample is measured with time from the start to the end of a blood coagulation reaction in order to monitor the blood coagulation reaction. Here, the optical change means a change in a scattered light amount, a transmitted light amount and the like. The blood coagulation reaction can be monitored by use of a blood coagulation analyzer, as described later, which is comprised mainly of a light-transmission container for accommodating the blood sample, a reagent supplier for supplying a blood coagulation reagent to the container, a light source for irradiating the accommodated blood sample with light, a photoreceptor for receiving light, e.g., scattered light, from the blood sample, a measuring section for measuring a change with time of the amount (or intensity) of the light, e.g., the scattered light, after the blood coagulation reagent is supplied to the blood sample and computing a blood coagulation time, and a display for displaying a result of computation by the measuring section.

The blood coagulation reaction can be analyzed from the monitored blood coagulation reaction to detect the presence or absence of abnormality in the blood coagulation reaction, especially in an initial stage of the blood coagulation reaction (first stage). The analysis of the reaction can be performed by setting a specific time point or range, or a specific optical change amount point or range as a checkpoint or a check region, for example in a coagulation reaction curve, from the start of the reaction to the end of the reaction, computing a reaction state (reaction rate, change amount, a time required for a specific change, etc.) at the set point or region and comparing the computed reaction state with a predetermined threshold value. The threshold value can be experimentally or empirically determined from tendency of normal samples or the like.

The analysis can be carried out, for example, on one or more of the following items:

(1) A reaction rate during fibrin formation (SLOW REACTION CHECK);

(2) The presence or absence of an initial stage of the blood coagulation reaction (START ANGLE CHECK);

(3) The presence or absence of a drift in a coagulation reaction curve (DRIFT CHECK); and (4) A time from the start of the reaction until the optical change amount reached a predetermined value (EARLY % CHECK).

These items are now explained in detail.

(1) A Reaction Rate During Fibrin Formation

In general, the optical change is very small before fibrin stars to form as a result of advances of the blood coagulation caused by the blood coagulation reagent introduced into the blood sample. However, once the fibrin formation starts and advances, a rapid optical change occurs within a short time. Therefore, by setting a checkpoint at a position of a specific change amount between the start of the optical change due to the fibrin formation and the end of coagulation, e.g., the fibrin formation, and checking the reaction rate at the checkpoint, abnormality can be detected. The reaction rate may be obtained by computing an optical change rate per unit time (inclination) at the checkpoint, or alternatively, by setting a specific range with the checkpoint as the center and counting a time required for producing the optical change of that range. A threshold is set for the reaction rate (the threshold can be set experimentally or experientially), and if the obtained reaction rate does not reach the threshold, it is judged that "a reaction rate abnormality" exists. In the case of the abnormality, an error flag may be set (for example, a sign such as asterisks "*" or a character such as "E") and displayed on the display section. This operation applies to the following items.

(2) The Presence or Absence of Initial Reaction

In general, there is little optical change amount at an initial stage of the coagulation reaction (for example, 20 seconds for APTT). By setting specific two time points as checkpoints during the initial stage of the reaction and obtaining the optical change amount of the duration between the two time points, the presence or absence of an initial stage of the reaction can be judged. A threshold is preset in the same manner as described above, and if the obtained optical change amount exceeds the preset threshold, it is judged that the initial stage of the reaction exists.

In addition to this, a threshold is set for the optical change amount from the start to the end of the fibrin formation. If this threshold is not met, it is judged that a measurement error exists, and the result is not to be reported. If the threshold is exceeded, the result may be reported and displayed with an error flag which indicates a measurement error.

(3) The Presence or Absence of Drift in Reaction Curve

In general, the rate of the optical change is little at the initial stage of the reaction, and the rate of the optical change is large during the fibrin formation. A significant difference is seen between the reaction rates at the initial stage of the reaction and during the fibrin formation. On the other hand, in a sample showing a gradual optical change, the reaction rates do not show so significant a difference as those of normal samples. Therefore, it is possible to check whether or not the optical change amount gradually increases (whether or not a drift exists) by comparing the reaction rates at the initial stage of the reaction and at the fibrin formation stage. Specifically, checkpoints are set at a position of a specific optical change amount at the initial stage of the reaction and at a position of a specific optical change amount at the fibrin formation stage, and the reaction rate at each point is obtained. Further, a ratio (the reaction rate at the initial stage of the reaction/the reaction rate during the fibrin formation) is computed. If the computed ratio does not meet a preset threshold, it is judged that a drift exists. The reaction rates can be obtained in the same manner as described previously.

(4) Checking Time Having Elapsed From the Start of the Reaction Until the Optical Change Amount Reached a Predetermined Value Generally, in normal samples, a relatively long time is required until the optical change takes place due to the fibrin formation. In contrast, in samples showing a gradual optical change, the optical change occurs immediately after or a relatively short time after the reagent is introduced into plasma. Therefore, a specific position of the optical change amount is set as a checkpoint, the time required for reaching the checkpoint is obtained, and the thus obtained time is compared with a preset threshold. Thereby it is possible to detect abnormality.

The abnormality of the reaction, especially the initial stage of the reaction can be detected with higher sensitivity by combining two or more of the above items (1) to (4). In particular, the method of the present invention is effective in APTT measurement.

The method of analyzing the blood coagulation reaction of the present invention is now described in detail with reference to the accompanying drawings.

Figure 3:
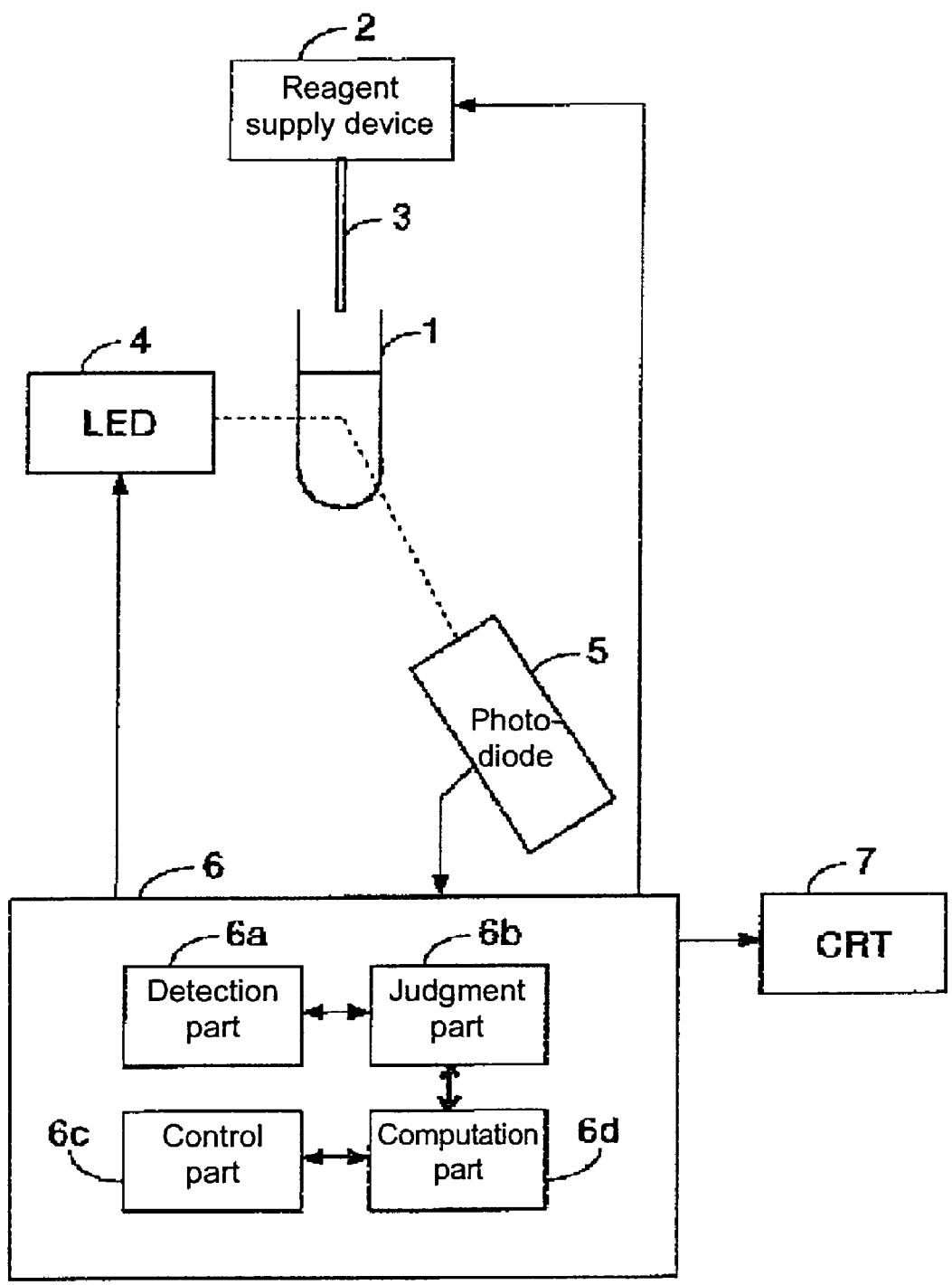
FIG. 3 is a view showing the constitution of a blood coagulation measuring apparatus.

The blood coagulation reaction is analyzed by use of a blood coagulation analyzer as shown in FIG. 3. In this blood coagulation analyzer, plasma to be analyzed is placed in advance in a transparent testing tube 1. When a reagent (for example, a PT reagent) is supplied from a reagent supply device 2 to the testing tube 1 via a pipette 3, light is emitted from an LED 4 to the testing tube 1. Light scattered inside the testing tube 1 is received by a photodiode 5, and the amount of the scattered light is detected.

A measuring section 6 is provided with a detection section 6a for detecting the amount of scattered light (change: increase, decrease or saturation); a judgment section 6b for judging whether or not the amount of scattered light increases; a control section 6c for, if saturation of the amount of scattered light is detected, judging whether or not the amount of scattered light further increases within a predetermined subsequent time and for, if the amount increases, controlling the detection section 6a and the judgment section 6b so that the detection of a subsequent saturation is repeatedly performed, and a computation section 6d for, when the saturation of the amount of scattered light is finally detected, computing a coagulation time based on a saturation value. The measuring section 6 is adapted to process an output signal of the photodiode 5 and display a processing result on a CRT 7.

Although the transparent testing tube 1 is used as the light transmission container in the above-described example, the light transmission container may be transparent at least at a portion involved in optical detection. For this purpose, a glass- or resin-made transparent testing tube or the like of 10 mm to 20 mm in diameter and 50 mm to 100 mm in height or the like, for example, may be used.

In the above-described example, the LED 4 is employed as the light source, for example. The photo-diode 5 is employed as the light receiver, but other devices such as a photo-transistor may be used as the light receiver. The CRT 7 is used as the display section, but the display section may be formed of a liquid crystal display and a device for printing the analysis results on printing paper as well. Furthermore, a microcomputer composed of a CPU, a ROM, and a RAM can be employed as the measuring section 6.

The detection section 6a may sequentially acquire and store values of the amount of scattered light at every predetermined time.

The judgment section 6b senses the start of the coagulation reaction, and then, i) may compute a difference between the most updated saturation value and the most updated acquisition value, whereby, when the difference is smaller than a first predetermined value, it may judge that the amount of scattered light does not increase (saturates). Or alternatively, ii) the judgment section 6b may compute a ratio of the difference between the most updated acquisition value and the minimum acquisition value to that between the most updated saturation value and the minimum acquisition value, whereby, when the ratio is smaller than a second predetermined value, it may judge that the amount of scattered light does not increase (saturates). In addition, iii) the judgment section 6b may compute the difference between the most updated saturation value and the most updated acquisition value and compute a ratio of the difference between the most updated acquisition value and the minimum acquisition value to the difference between the most updated saturation value and the minimum acquisition value, whereby, when the difference is smaller than the first predetermined value and when the ratio is smaller than the second predetermined value, it may judge the amount of scattered light does not increase. When the saturation of the amount of scattered light has been detected, it is monitored whether or not the amount of scattered light does not further increase for a predetermined time. When the amount increases again, the detection of the saturation of the amount of scattered light is repeated to detect the final saturation value. Thereby, even in the case where the reaction looks as if it stops temporarily on its way, the computation section 6d can determine the coagulation time more precisely. Further, after the final saturation value is determined, the judgment section 6b may preferably analyze the advance of the coagulation reaction and, if a predetermined condition is met, judge an initial reaction abnormality. Here the saturation means that the change of the amount of scattered light with time disappears temporarily or permanently.

EXAMPLE 1

Figure 4:
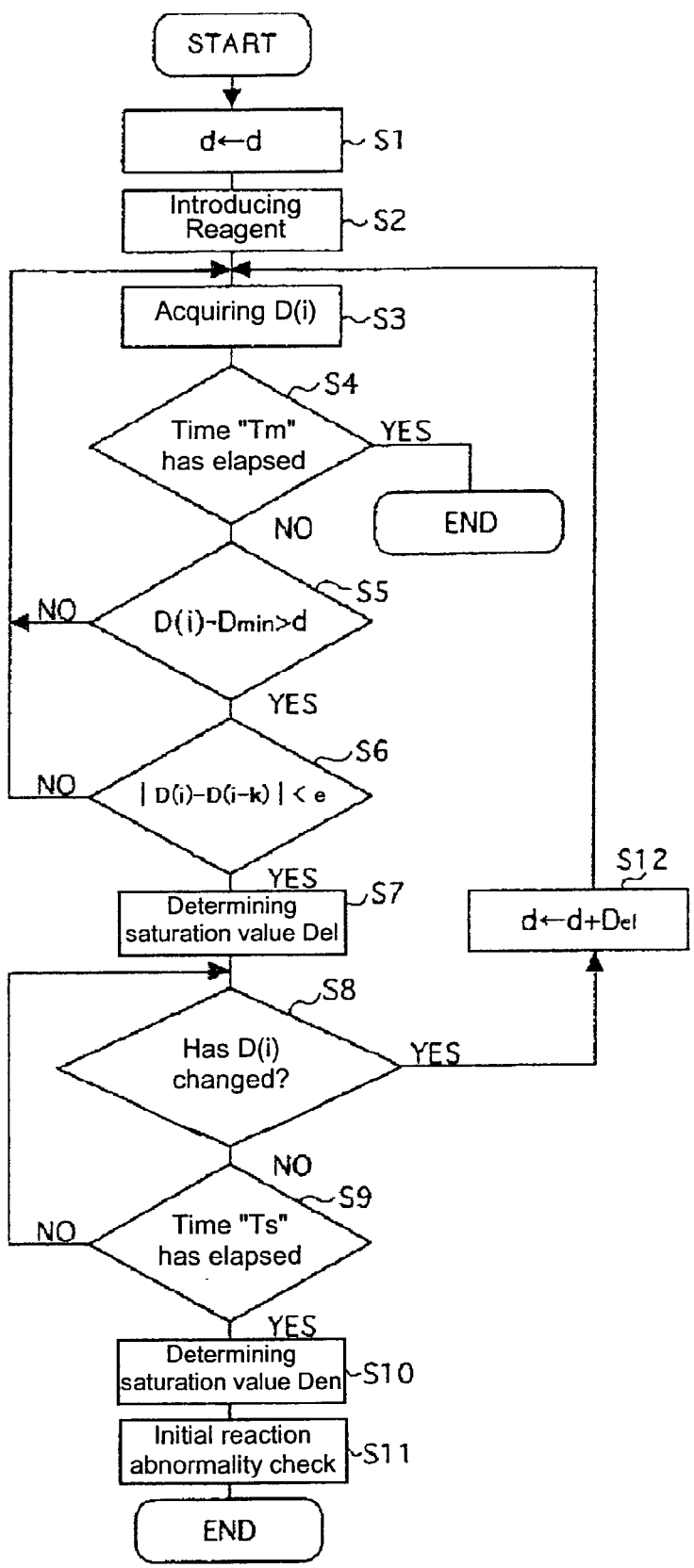
FIG. 4 is a flowchart showing the computation of a coagulation time by the blood coagulation measuring apparatus.

A general procedure of the blood coagulation analyzing method is further described in detail with reference to a flowchart shown in FIG. 4.

First, in step S1, initial setting is provided. Next, when a reagent is supplied from the reagent supplying device 2 in accordance with an instruction from the measuring section 6, the LED 4 is lit at the same time. Then, a current amount of scattered light D(i) is acquired from the photodiode 5, and measurement is started (steps S2 and S3). Acquisition of the amount of scattered light is performed on every 0.1 second, for example.

Next, if a preset maximum measurement time Tm (for example, 600 seconds) does not elapse from the start of measurement in step S4, a difference between the minimum value Dmin among values acquired so far and a current value D(i) is computed. If the difference is greater than an initially set value "d", it is judged that a change has occurred with the acquired value, namely, that coagulation reaction has started (step S5). Every time when a current value D(i) is acquired, a difference between the current value D(i) and the value D(i-k) acquired at the measurement "k" times before is computed (wherein k=1, 2, 3, . . . 63). When the difference is smaller than a predetermined value "e" (step S6), D(i) at this time is regarded as a tentative saturation value "Del" (step S7).

Then, every time when a current value D(i) is acquired, a difference between D(i) and Del and a ratio of (D(i)−Dmin) to (Del−Dmin) are computed. If the difference is smaller than a predetermined value "f" and the ratio is smaller than 1.2, it is regarded that the current value D(i) does not change (saturates) (step S8).

When this unchanged state has continued for a predetermined time "Ts" (for example, 100 seconds) (step S9), the saturation value "Del" is determined to be a final saturation value "Den" (step S10).

Figure 5:
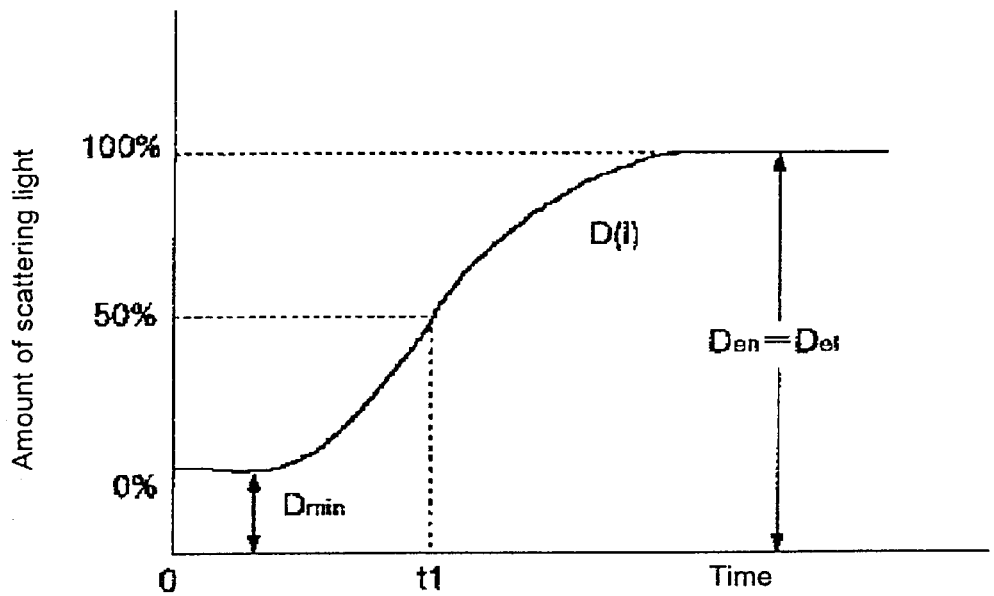
FIG. 5 is a view showing a change with time in the amount of scattered light in an example.

FIG. 5 is a graph depicting the above described process. As shown in FIG. 5, when "Den" is taken as 100% and "Dmin" is taken as 0%, a time "t1" when the amount of scattered light reaches 50% is computed as a coagulation time. Then, the graph of FIG. 5 and the value of "t1" are displayed on the CRT 7.

Next, when D(i) has changed in the step S8, "d" is reset to (d+Del), and the routine reverts to the step S3. Then, the steps S3 to S8 are repeated. When it is regarded that D(i) does not change (saturates) even after the time "Ts" has elapsed (step S9), the saturation value "Del" is determined to be a final saturation value "Den" (step S10). However, in the step S4, if time after the start of measurement exceeds "Tm", the measurement is terminated, and "immeasurable" is displayed on the CRT 7.

When the final saturation value "Den" is determined, an initial reaction abnormality check (step S11) is then performed at the judgment section as follows. If it is judged that no abnormality occurs, the coagulation time is computed. If it is judged that abnormality occurs, an error flag is set and displayed on the CRT 7.

EXAMPLE 2

A procedure of analyzing the blood coagulation reaction of an abnormal sample which produces an optical change immediately after the introduction of the reagent (immediately after the reaction has started) is now explained with reference to the flowcharts of FIGS. 6 to 9 and FIGS. 10 to 13. The blood coagulation reaction in this explanation is carried out using an APTT reagent for measuring APTT. For simplicity of explanation, FIGS. 6 to 9 shows not only an optical change amount (amount of scattered light change) $\Delta H$ (=Den−Dmin) from an un-coagulated level to a coagulation endpoint of an abnormal sample but also that of a normal sample.

(1) The Presence or Absence of Abnormality of the Reaction Rate During the Fibrin Formation (SLOW REACTION CHECK)

Figure 6:
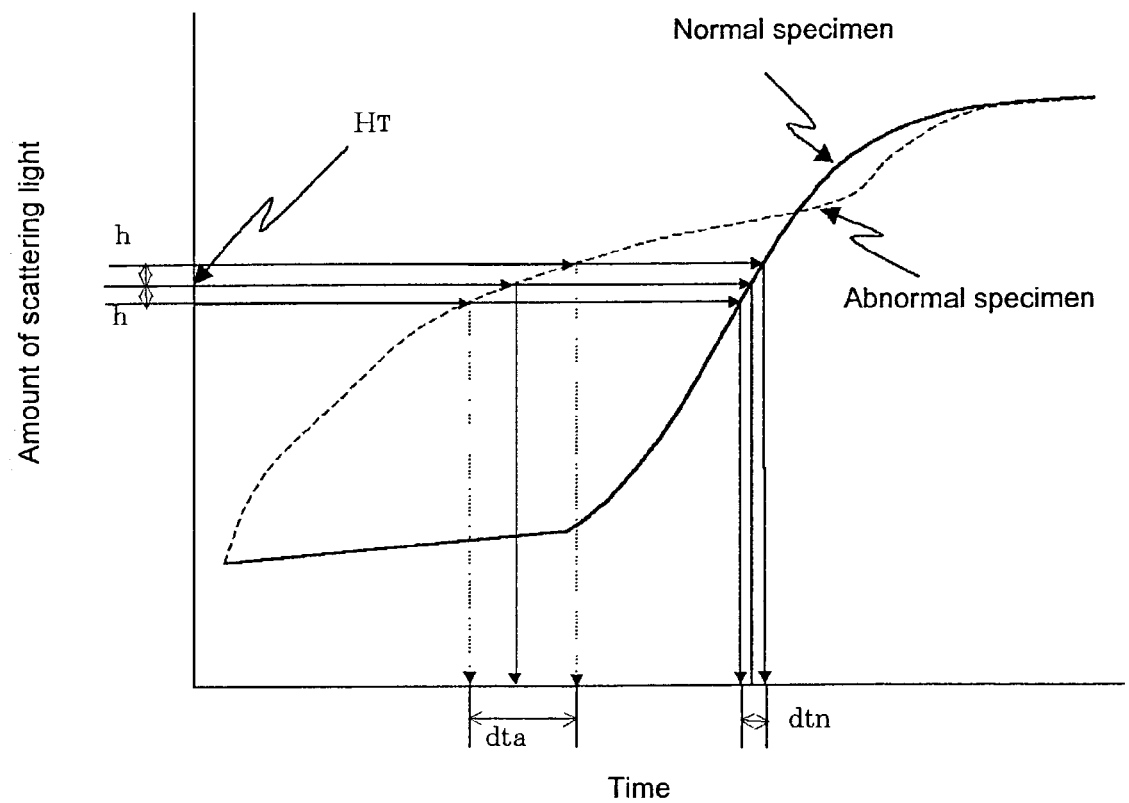
FIG. 6 is a view illustrating the detection of a reaction rate abnormality of the fibrin formation stage.
Figure 10:
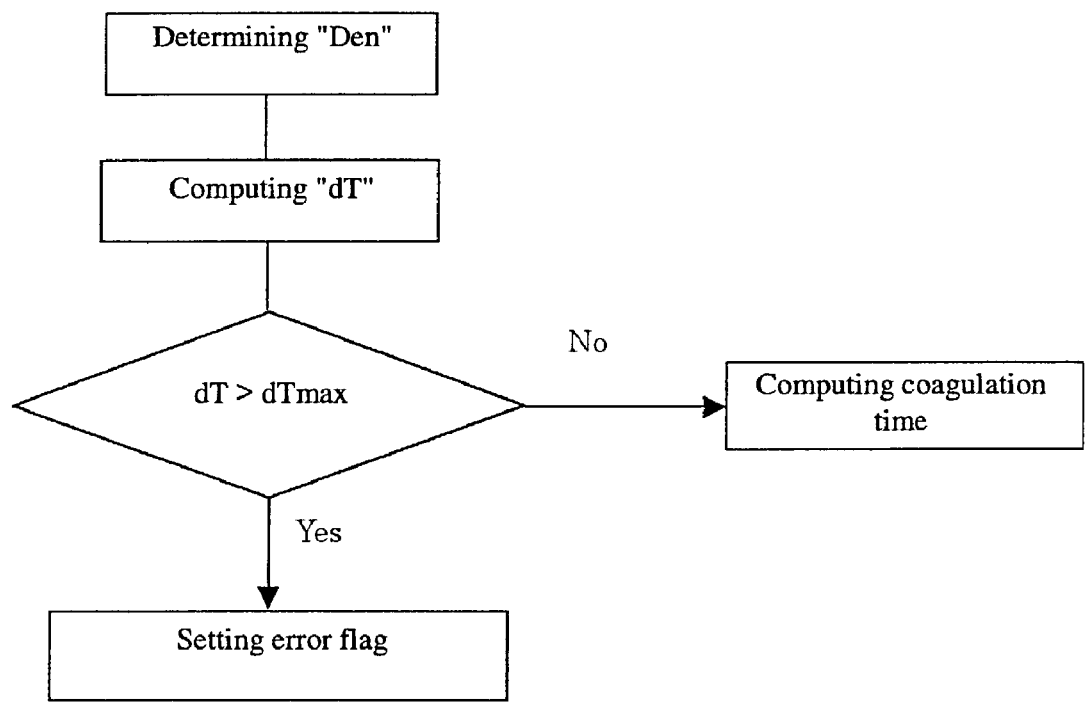
FIG. 10 is a flowchart illustrating the detection of a reaction rate abnormality of the fibrin formation stage.

As shown in FIG. 6, the blood coagulation reaction is measured, and a blood coagulation reaction curve is generated. Then, as shown in the flowchart of FIG. 10, the final saturation value Den of the amount of scattered light at the coagulation endpoint is determined about the abnormal sample.

Subsequently, in FIG. 6, a checkpoint $H_T$ is first preset. Although $H_T$ can be arbitrarily determined, the checkpoint $H_T$ may preferably be set at a point exhibiting around 50% of the total scattered light change amount because the reaction rates of the normal sample and the abnormal sample tend to differ easily from each other. Next, a window with a width of "h" is set to have $H_T$ at the center (i.e., symmetric window). The value of "h" can be arbitrarily set. For example, if $H_T$ is 50% and "h" is 4%, a time "dT"=$T_{54\%}$-$T_{46\%}$ required for a change of the amount of scattered light of the range of 46% to 54% (where $T_{54\%}$ is a time required for a change up to 54%, and $T_{46\%}$ is a time required for a change up to 46%) is obtained.

A time "dta" necessary for the abnormal sample to produce the change of the amount of scattered light of the window is longer than the time "dtn" necessary for the normal sample to produce the change of the amount of scattered light of the window. Therefore, a threshold dTmax (dTmax can be determined experimentally or experientially) is preset, and if dT>dTmax is met, it is judged as abnormality. Once the abnormality is judged, an error flag can be set and displayed.

(2) The Presence and Absence of the Initial Reaction (START ANGLE CHECK)

Figure 7:
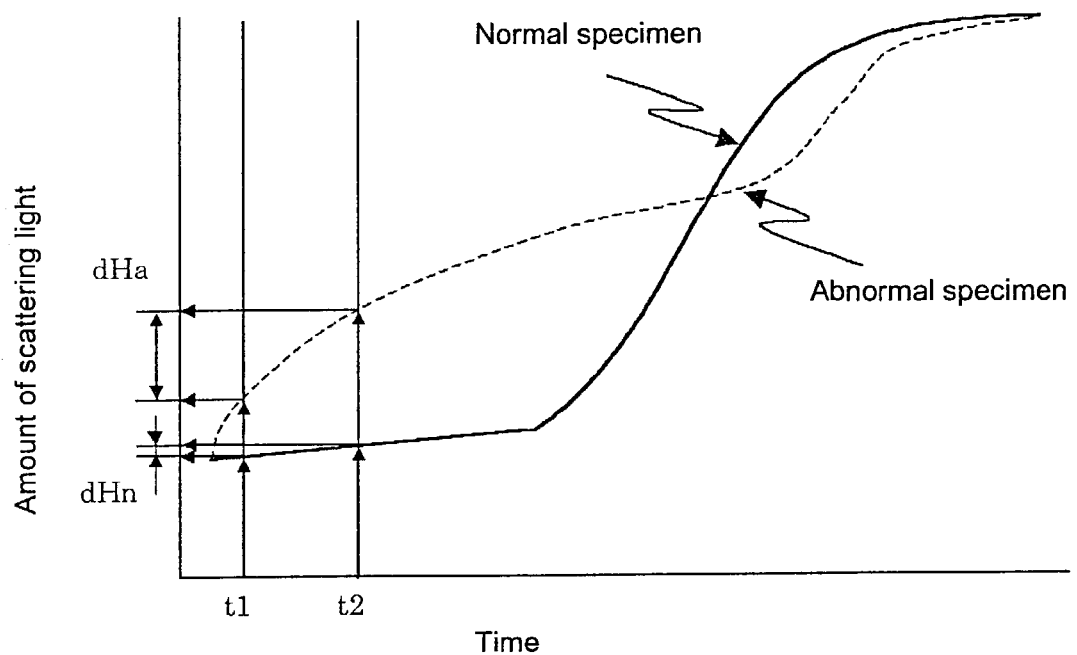
FIG. 7 is a view illustrating the detection of the presence or absence of an initial stage of the blood coagulation reaction.
Figure 11:
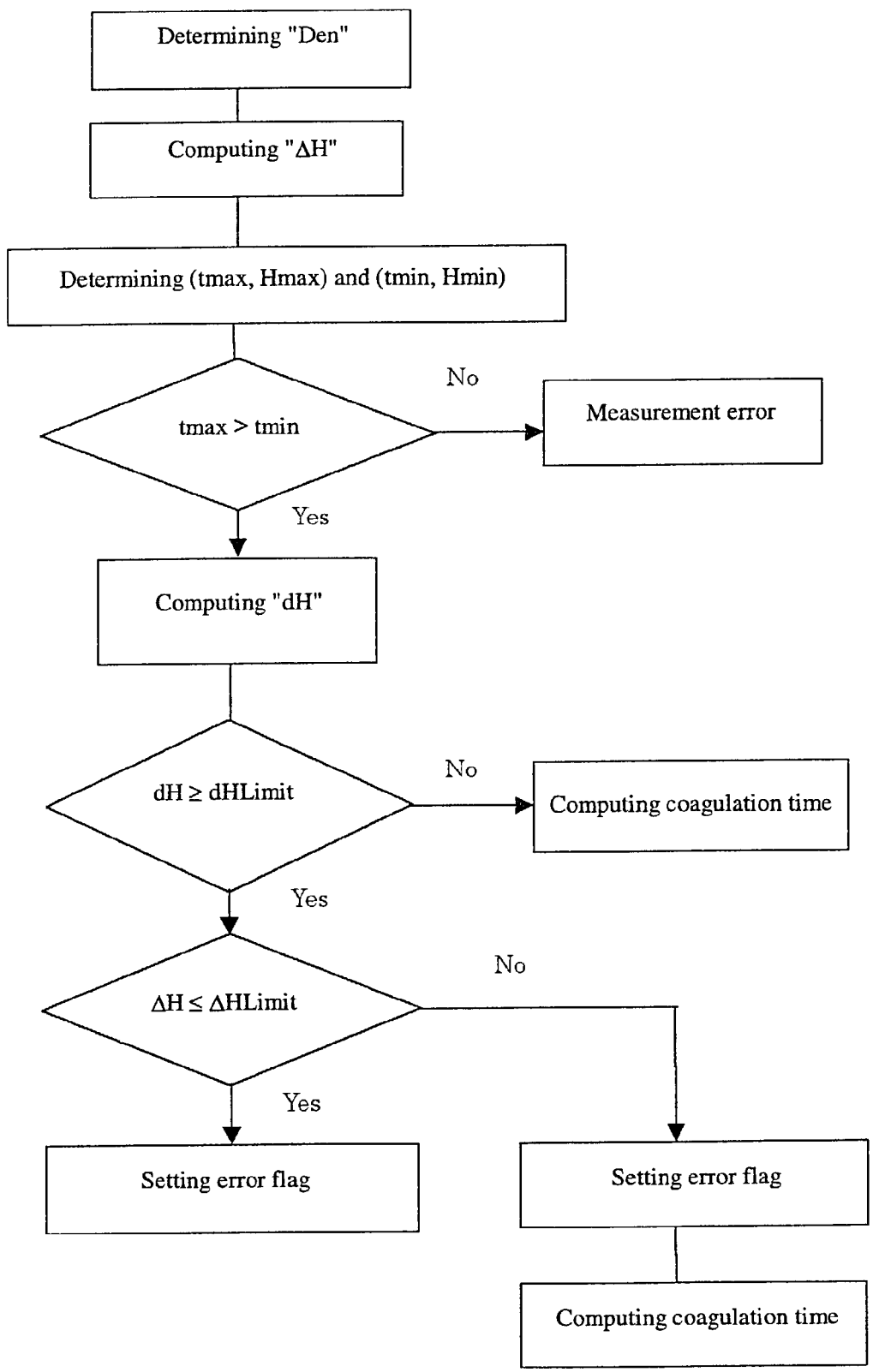
FIG. 11 is a flowchart illustrating the detection of the presence or absence of abnormality in an initial stage of the blood coagulation reaction.

As shown in FIG. 7, the blood coagulation reaction is measured, and a blood coagulation reaction curve is generated. Then, as shown in the flowchart of FIG. 11, the final saturation value Den of the amount of scattered light at the coagulation endpoint is determined about the abnormal sample, and a change amount $\Delta H$ in the amount of the scattered light is calculated.

Subsequently, in FIG. 7, a first time point t1 and a second time point t2 are preset in a time interval of the initial stage of the reaction (about 20 seconds for APTT), and an interval between "t1" and "t2" is defined as a check region. Within the region, a search is made for a point ($t_{max}$, $H_{max}$) of a maximum value ($H_{max}$) in change of the amount of scattered light and a point ($t_{min}$, $H_{min}$) of a minimum value ($H_{min}$) in the change of the amount of scattered light. If there exist a plurality of points of the maximum value, the one of these points having the maximum time is defined as ($t_{max}$, $H_{max}$). In addition, if there exist a plurality of points of the minimum value, the one of these points having the minimum time can be defined as ($t_{min}$, $H_{min}$). In the example of FIG. 7, $t_{min}$=t1 and $t_{max}$=t2 are obtained, and the change amounts of scattered light at these points are defined as $H_{min}$ and $H_{max}$, respectively.

Next, the change amount of scattered light dH=$H_{max}$-$H_{min}$ in the check region is computed. The change amount of scattered light dHa in the abnormal sample is larger than the change amount dHn of scattered light in the normal sample. Therefore, a threshold $dH_{Limit}$ is set, and if dH≧$dH_{Limit}$ is met, it is judged as abnormality. Then, an error flag is set and displayed on the display section.

In addition, a threshold $\Delta H_{Limit}$ is set for the change amount of scattered light ΔH from the start of the reaction to the endpoint of the coagulation, and, if dH≧$dH_{Limit}$ and $t_{max>tmin}$ and ΔH≦$\Delta H_{Limit}$ hold, it is regarded that the initial reaction is found, and moreover, that a sufficient optical change amount due to the fibrin formation does not occur. Then, an error flag is set to indicate a measurement error and is displayed on the display section. If dH≧$dH_{Limit}$ and $t_{max>tmin}$ and ΔH>$\Delta H_{Limit}$, it is judged that the initial reaction is found but that a sufficient optical change amount exists. Then, an error flag is set to indicate a measurement error. Further, the coagulation time is computed, and the result is displayed. In the case of dH<$dH_{Limit}$, it is judged that no initial reaction occurs. Then, the coagulation time is computed, and the result is displayed.

(3) Presence or Absence of a Drift in a Reaction Curve (DRIFT CHECK)

Figure 8:
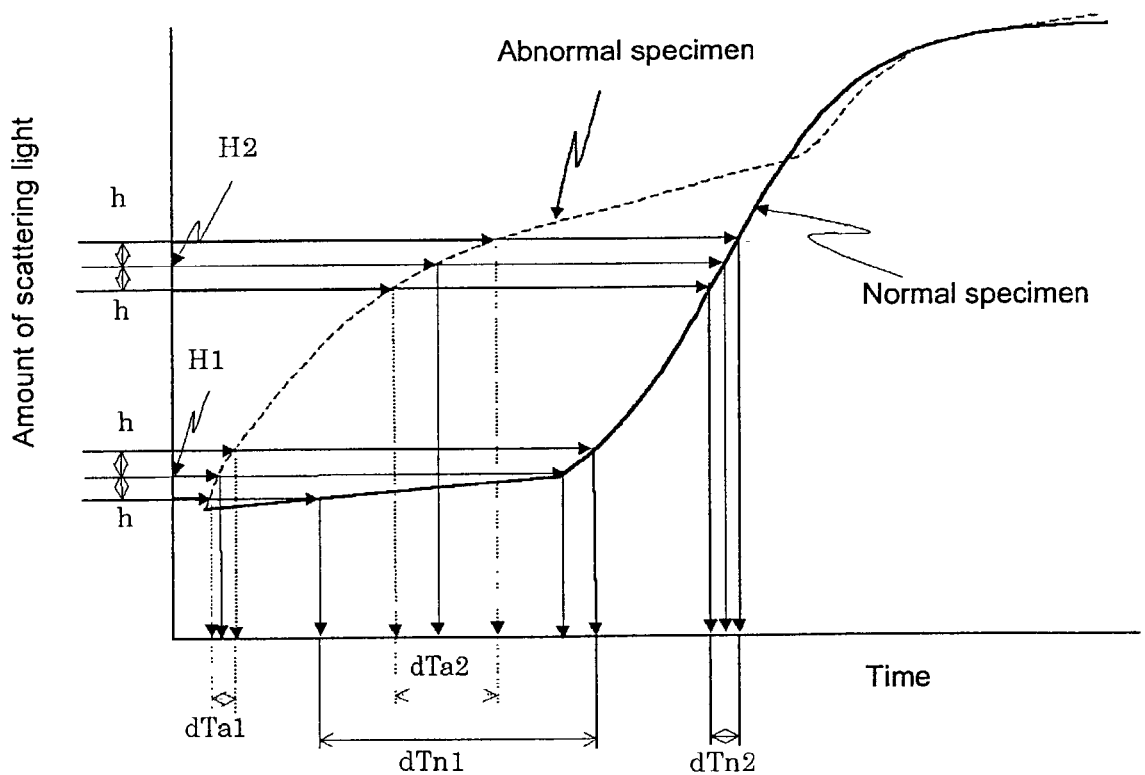
FIG. 8 is a view illustrating the detection of the presence or absence of a drift in a reaction curve.
Figure 12:
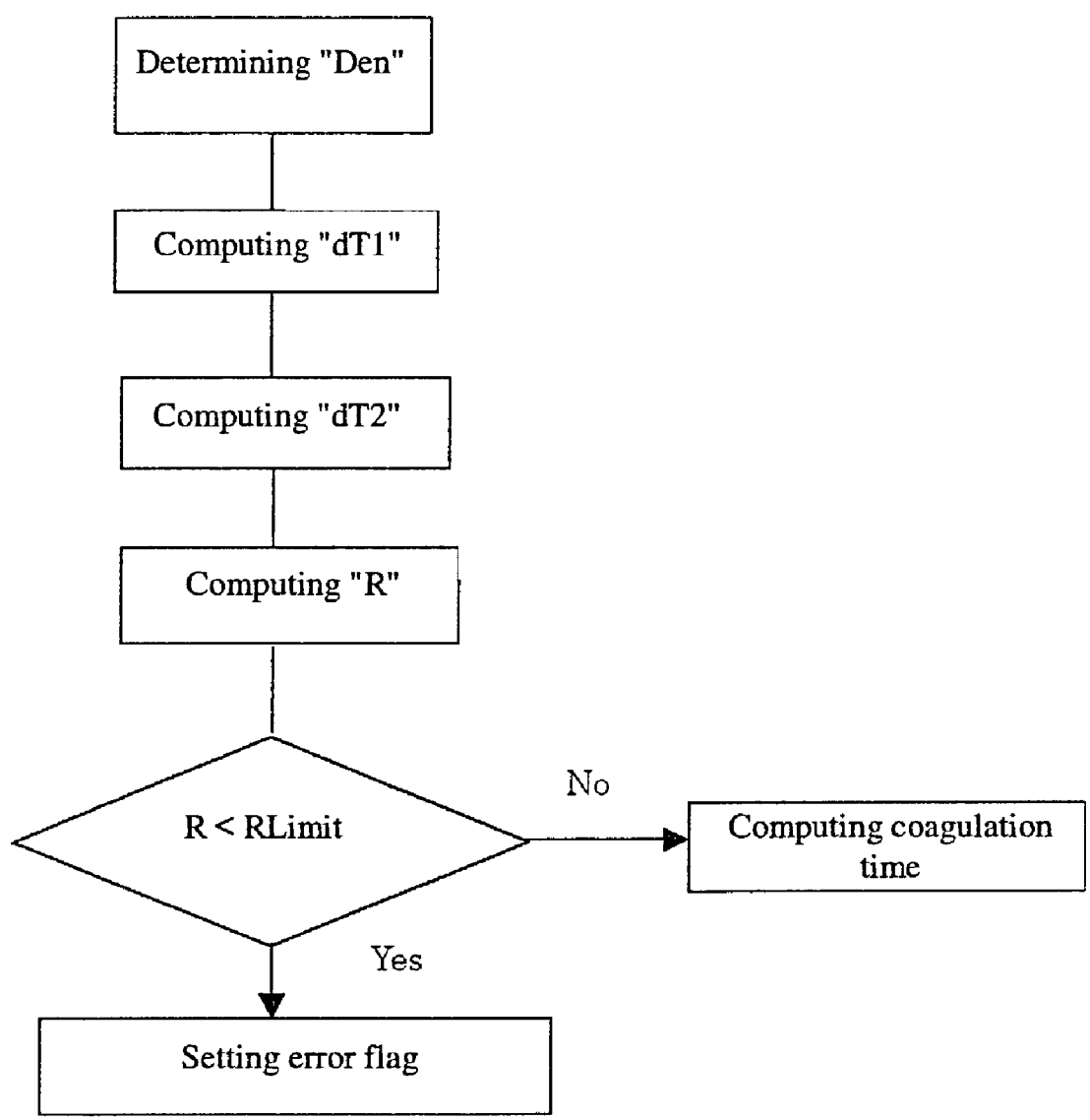
FIG. 12 is a flowchart illustrating the detection of the presence or absence of a drift in a reaction curve.

As shown in FIG. 8, the blood coagulation reaction is measured, and a blood coagulation reaction curve is generated. Then, as shown in the flowchart of FIG. 12, the final saturation value Den of the amount of scattered light at the coagulation endpoint is determined about the abnormal sample.

Subsequently, in FIG. 8, a first checkpoint H1 is preset at a position of the amount of scattered light at the initial stage of the reaction, and a second checkpoint H2 is preset at a position of the amount of scattered light during the fibrin formation. H1 and H2 can be arbitrarily determined. Next, windows with a width of "h" are set to have the respective checkpoints H1 and H2 at their centers. A value of "h" can be arbitrarily set. For example, in the case where H1=10%, H2=50% and h=4%, windows ranging from 6% to 14% and 46% to 54% are set. Next, times dT1=$T_{14\%}$-$T_{6\%}$ (wherein $T_{14\%}$ is a time required for a change up to 14%, and $T_{6\%}$ is a time required for a change up to 6%) and dT2=$T_{54\%}$-$T_{46\%}$ (where $T_{54\%}$ is a time required for a change up to 54%, and $T_{46\%}$ is a time required for a change up to 46%) are obtained as time required for the changes of the amount of scattered light in the windows. Further, the ratio of reaction rates at two checkpoints R=dT1/dT2 is computed. As compared with Rn=dTn1/dTn2 of the normal sample (where Rn is the ratio of the reaction rates in the normal sample, dTn1 is a time required for a change of the amount of scattered light at the first checkpoint, and dTn2 is a time required for a change of the amount of scattered light at the second checkpoint), Ra=dTa1/dTa2 of the abnormal sample (where Ra is the ratio of the reaction rates in the abnormal sample, dTa1 is a time required for a change of the amount of scattered light at the first checkpoint, and dTa2 is a time required for a change of the amount of scattered light at the second checkpoint) is smaller. Therefore, a threshold $R_{Limit}$ is set, and if R<$R_{Limit}$ is met, it is judged that a drift exists (i.e., the reaction curve is not flat, and rises gradually). Then, an error flag is set and displayed on the display section.

(4) Time Until a Preset Optical Change Amount Has Been Reached (EARLY % CHECK)

Figure 9:
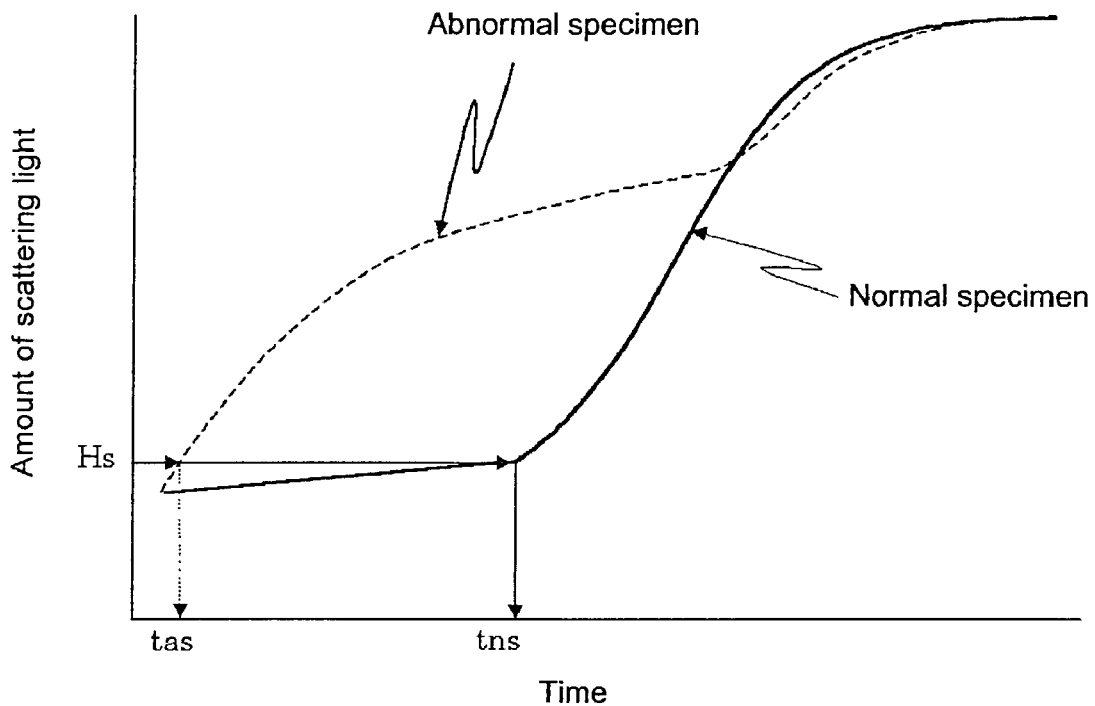
FIG. 9 is a view illustrating the detection of an abnormality of a time until a predetermined optical change amount has been reached.
Figure 13:
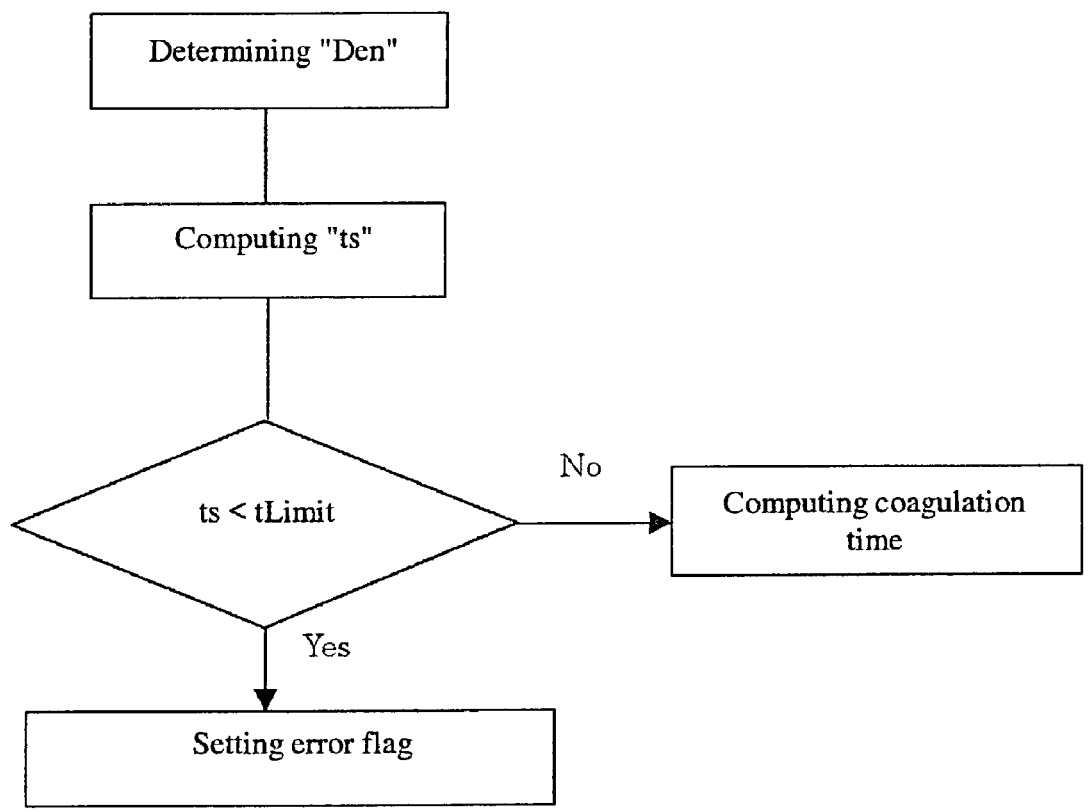
FIG. 13 is a flowchart illustrating the detection of an abnormality of a time until a predetermined optical change amount has been reached.

As shown in FIG. 9, the blood coagulation reaction is measured, and a blood coagulation reaction curve is generated. Then, as shown in the flowchart of FIG. 13, the final saturation value Den of the amount of scattered light at the coagulation endpoint is determined about the abnormal sample.

In FIG. 9, a checkpoint Hs of a specific change amount of scattered light is preset. This check item is for monitoring whether or not the time when the amount of scattered light starts to change is too early. It is preferable that "Hs" is set at a position at which the amount of scattered light starts to change. Next, a time "ts" required for the amount of scattered light to change to "Hs" is obtained. As compared with "tns" of the normal sample (where "tns" is a time required for the amount of scattered light to change to Hs in the normal sample), "tas" of the abnormal sample (where "tas" is a time required for the amount of scattered light to change to "Hs" in the normal sample) is small. Therefore, a threshold $t_{Limit}$ is preset, and if ts<$t_{Limit}$, it is judged that the time when the amount of scattered light starts to change is too early. Then, an error flag is set and displayed on the display section.

In accordance with the present invention, abnormality can be detected accurately in the blood coagulation reaction, especially, in the initial reaction. Consequently, it is possible to perform accurate measurement of the blood coagulation time by utilizing the blood coagulation reaction.

Also, abnormality can be closely detected in various reaction systems regarding the blood coagulation reaction. More particularly, it is possible to recognize abnormality in the reaction rate during the fibrin formation, to judge the presence of the initial reaction and the presence of the drift in the coagulation reaction curve and to recognize abnormality in the time from the start of the reaction until the predetermined optical change amount is reached, and the like. The results of the detection of such abnormality can be clinically utilized.

What is claimed is:
1. An analyzing method of a blood coagulation reaction by detecting an optical change of a blood sample with an elapse of time, the method comprising the steps of:
   setting a checkpoint or check region between the start of the reaction and the end of reaction, and monitoring a reaction state of the reaction by:
   computing a check item at the checkpoint or check region;
   comparing the check item with a predetermined threshold value; and
   judging the presence or absence of abnormality of the blood coagulation reaction based on the compared result;
   wherein the check item is selected from the group consisting of a first item, a second item, a third item and a fourth item, the first item being a first time required for changing from a first optical detecting value to a second optical detecting value, the second item being an amount of optical change in a predetermined time range, the third item being a ratio between a second time required for changing from a third optical detecting value to a fourth optical detecting value and a third time required for changing from a fifth optical detecting value to a sixth optical detecting value, and the fourth item being a fourth time required for reaching a predetermined optical detecting value.

2. The method of claim 1, wherein the coagulation reaction starts by mixing the blood sample with a blood coagulation reagent.

3. The method of claim 1, wherein the checkpoint and check region are shown based on a coagulation reaction curve represented by the optical change with the elapse of time.

4. The method of claim 1, wherein the predetermined threshold value is a first threshold value, and the judging step judges a presence or absence of abnormality of a reaction rate of fibrin formation stage in the blood coagulation reaction based on the compared result of the first item and the first threshold.

5. The method of claim 1, wherein the predetermined threshold value is a second threshold value, and the judging step judges a presence or absence of an initial stage in the blood coagulation reaction based on the compared result of the second item and the second threshold.

6. The method of claim 1, wherein the predetermined threshold value is a third threshold value, and the judging step judges a presence or absence of a drift in a coagulation reaction curve represented by the optical change with the elapse of time based on the compared result of the third item and the third threshold.

7. The method of claim 1, wherein the judging step judges whether or not the blood sample is an abnormal sample based on the judgment of the presence or absence of abnormality.

8. The method of claim 1, wherein, when the check item is the first item, a point exhibiting 50% of the total optical change amount exists between the first optical detecting value and the second optical detecting value.

9. The method of claim 1, wherein the predetermined time range is a time interval of the initial stage of the blood coagulation reaction.

10. The method of claim 1, wherein, when the check item is the third item, a point exhibiting 50% of the total optical change amount exists between the fifth optical detecting value and the sixth optical detecting value, and a point exhibiting 10% of the total optical change amount exists between the third optical detecting value and the fourth optical detecting value.

11. The method of claim 1, further comprising a step of displaying an error based on the compared result.

12. The method of claim 1, further comprising a step of measuring a blood coagulation time based on the blood coagulation reaction.

* * * * *